United States Patent
Ponomarenko et al.

(10) Patent No.: US 8,333,746 B2
(45) Date of Patent: Dec. 18, 2012

(54) DISPOSABLE ABSORBENT ARTICLE WITH SEPARATE PART

(75) Inventors: Ekaterina Anatolyevna Ponomarenko, Bad Soden (DE); Maja Wciorka, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 842 days.

(21) Appl. No.: 12/030,466

(22) Filed: Feb. 13, 2008

(65) Prior Publication Data

US 2008/0195073 A1 Aug. 14, 2008

(30) Foreign Application Priority Data

Feb. 13, 2007 (EP) .................................... 07102195

(51) Int. Cl.
*A61F 13/15* (2006.01)

(52) U.S. Cl. ......... 604/385.01; 604/385.03; 604/385.11; 604/385.14

(58) Field of Classification Search ................... 604/327, 604/348, 385.03, 385.08, 385.14, 385.19, 604/396, 400–402, 385.01, 385.11, 386
See application file for complete search history.

(56) References Cited

U.S. PATENT DOCUMENTS

| | | | | |
|---|---|---|---|---|
| 1,329,119 | A * | 1/1920 | George | 604/394 |
| 4,597,760 | A * | 7/1986 | Buell | 604/397 |
| 5,207,663 | A | 5/1993 | McQueen | |
| 5,322,729 | A | 6/1994 | Heeter et al. | |
| 5,792,132 | A * | 8/1998 | Garcia | 604/385.01 |
| 5,876,394 | A * | 3/1999 | Rosch et al. | 604/393 |
| 5,876,753 | A | 3/1999 | Timmons et al. | |
| 5,888,591 | A | 3/1999 | Gleason et al. | |
| 6,045,877 | A | 4/2000 | Gleason et al. | |
| 6,913,599 | B2 * | 7/2005 | Mishima et al. | 604/385.08 |
| 6,989,005 | B1 * | 1/2006 | LaVon et al. | 604/385.14 |
| 7,344,526 | B2 * | 3/2008 | Yang et al. | 604/393 |
| 7,678,093 | B2 * | 3/2010 | Nordness et al. | 604/385.08 |

(Continued)

FOREIGN PATENT DOCUMENTS

EP 1 201 212 A2 5/2002

(Continued)

OTHER PUBLICATIONS

International Search Report PCT/IB2008/050528 mailed Jun. 30, 2008.

*Primary Examiner* — Nicholas D Lucchesi
*Assistant Examiner* — Benedict L Hanrahan
(74) *Attorney, Agent, or Firm* — Charles R. Matson; Matthew P. Fitzpatrick (57) ABSTRACT

A disposable absorbent article is disclosed including an inner part including a sheet of material having an inner side, an outer side opposite the inner side, a front waist region, and a rear waist region, wherein the front waist region is connected with the rear waist region to form a waist opening and two leg openings; an outer part including an absorbent material, the outer part being separate from the inner part and adapted to be worn over the outer side of the inner part such that the inner part can be worn independently of the outer part; and an opening in the sheet of material of the inner part for allowing bowel movement waste to pass through the opening so that the inner part cooperates with the outer part in use to collect and retain bowel movement waste between the inner and outer parts.

10 Claims, 5 Drawing Sheets

| U.S. PATENT DOCUMENTS | | | |
|---|---|---|---|
| 2005/0010185 A1 | 1/2005 | Mizutani et al. | |
| 2008/0119812 A1 * | 5/2008 | Hurwitz | 604/385.23 |

FOREIGN PATENT DOCUMENTS

| EP | 1 214 921 A1 | 6/2002 |
|---|---|---|
| WO | WO 96/00549 | 1/1996 |
| WO | WO 96/03501 | 2/1996 |
| WO | WO 9843574 A1 * | 10/1998 |
| WO | WO 2005/112854 A | 12/2005 |

* cited by examiner

DISPOSABLE ABSORBENT ARTICLE WITH SEPARATE PART

CROSS REFERENCE TO RELATED APPLICATIONS

This application claims priority to European Patent Application No. EP07102195.0, filed Feb. 13, 2007, which is hereby incorporated by reference.

FIELD OF THE INVENTION

The present disclosure is directed to disposable absorbent articles, such as diapers, training pants, adult incontinence articles, feminine protective articles and the like, in a two part form having an outer absorbent part cooperating with a separate inner part to receive viscous bodily waste such as bowel movement waste, here referred to as BM.

BACKGROUND OF THE INVENTION

Before the introduction of modern absorbent diapers, a combination of outer plastic pants and washable, absorbent inner diapers were used to collect and retain body exudates from babies. The inner diapers were frequently of cotton or other similar absorbent material and were held in place using safety pins.

Such products have been largely replaced by disposable absorbent diapers. A conventional modern diaper structure may include a backsheet, a topsheet and an absorbent core between the topsheet and backsheet, as well as many other components such as elasticated cuffs, stretchable regions, and various other components intended in improve performance. Such conventional diapers may be provided with a front waist region and a back waist region that are joined by a carer to form a waistband. An alternative configuration is the "pants-type" diapers which has the front waist region and back waist region already joined in the product as sold—such training pants can be put on in a similar way to conventional underwear.

Similar structures are known for adult incontinence products and other similar uses.

A problem with such conventional absorbent articles is to deal with body emissions that are not liquid, including for example BM.

In order to try to minimize the escape of BM and reduce soiling of the skin by BM trapped in the diaper, apertures have been provided in the topsheet to allow feces to pass into a void space between the topsheet and underlying layers of the diaper. However, such apertures can be difficult to position during application of the absorbent article and are particularly difficult to maintain in position as the article is worn. In spite of many different attempts, prior art diapers with such apertures tend not to have good performance.

A prior proposal is made by U.S. Pat. No. 5,207,663 in which a protective article for bowel incontinence is described. The protective article includes a double panel pouch at the rear of the article suspended from the waistband. An elasticized slit is provided on the inner panel of the pouch adjacent to the wearer's anus to admit fecal matter directly into the pouch.

However, articles including such a separate pouch are much more difficult and expensive to manufacture than conventional diapers since additional layers need to be mounted and aligned.

A more recent and more successful diaper with an opening is described in European Patent Publication EP1201212A2. Elastic regions extend longitudinally on either side of a central opening which provides a passage to an integral void space for receiving body exudates.

However, such a diaper is still not straightforward to manufacture in view of the number of different components that need to be brought together and aligned.

SUMMARY OF INVENTION

It has been realized that by providing a separate inner part many of the manufacturing difficulties involved in producing an absorbent article with an integral inner layer having an opening can be avoided. Even though the inner and outer parts are separate, so there is no closed pouch or pocket, the inner part can significantly reduce soiling. The alignment of inner and outer parts may be achieved by both being worn by the user. The aperture in the inner part may be held in place by elastic regions extending longitudinally on either side of the opening. In use, the elastic regions and slit pass between leg openings. In another aspect, the inner part has a fastening means that may be adapted to fix the inner part in place around a wearer or to fix the inner part to an outer part.

BRIEF DESCRIPTION OF DRAWINGS

The Figures are schematic and not to scale. The same or similar components are given the same reference numerals in different embodiments, and the description of such components is not generally repeated.

DETAILED DESCRIPTION OF THE INVENTION

As used herein, the following terms have the following meanings:

An "absorbent article" refers to a wearable device, which absorbs and/or contains liquid and in particular to devices placed against or in proximity of the body of a wearer to absorb and contain the various exudates discharged from the body.

A "diaper" as used herein refers to an absorbent article worn generally by infants and incontinent persons about the lower torso.

"Non-absorbent" refers to a component that does not contain any material of the type that may be used to absorb significant quantities of fluid or other bodily waste.

"Longitudinal" refers to a direction in a diaper running parallel to the maximum linear dimension of the article, typically the longitudinal axis. The term "along the longitudinal axis" includes directions within 45° of this axis. The "length" of an article or component generally refers to the size of the article or components in the direction of the longitudinal axis "Lateral" refers to a direction generally orthogonal to the longitudinal direction in the same plane as the article. The "width" of an article or component generally refers to the size of the article or components in this lateral direction orthogonal to the length.

"Thickness" refers to the direction and length generally orthogonal to both longitudinal and lateral direction, i.e. when referring to a sheet the direction normal to the plane of the sheet. The thickness may also be referred to as the caliper. The thickness or caliper is measured at 0.3 psi, i.e. a pressure of 2068 Pa.

The "Mid Point" as used herein of an article or component is the mid-point of the longitudinal axis, i.e. the mid-point of the centre line of the article for a symmetric article or component.

"Elastic" as used herein refers to any component, part, or region which may be stretched and which, on release of the stretching force, returns at least in part towards its unstretched state.

"Elasticated" as used herein refers to any elastic component part or region created by adding an elastic component, sheet or the like to another component, whether or not the other component is itself elastic.

Two components are said to be "permanently attached" when they are joined in a way that the components cannot be separated without causing damage.

"Separate" means not permanently fixed together. Two components are separate if they are either not fixed together at all or fixed together in a way that the components can be separated without damage to either component.

Figure 1:
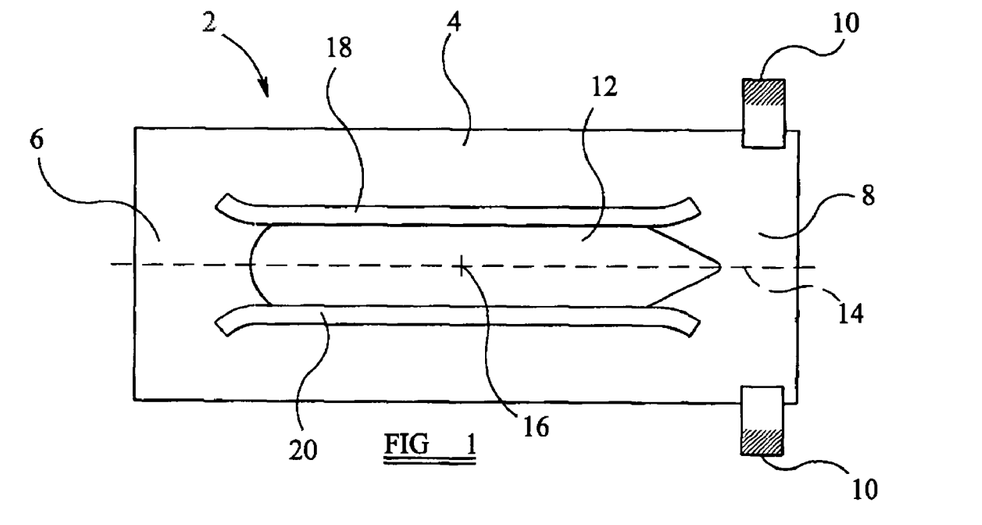
FIG. 1 shows a side view of a first embodiment of a diaper-type elasticated inner part as worn by a baby.

FIG. 1 shows a first embodiment a diaper-type inner part 2 in flat form. The outside of the inner part, i.e. the side intended to face away from the wearer, is shown in the Figure.

The inner part 2 is formed of a sheet 4 of nonwoven material. The sheet 4 may act as a barrier to BM, i.e. it is capable of containing BM. The properties of the sheet may be substantially the same regardless of where they are measured, except where additional components are attached.

In an embodiment, the sheet 4 is formed of a non-woven. In the embodiment, the non-woven is hydrophobic. The non-woven may be a high barrier non-woven material that substantially prevents liquid and solid from passing through it. The inner part has longitudinally spaced front 6 and rear 8 waist regions and fastening means 10 that are adapted to fix the front and rear waist portions together in use. The sheet 4 may be non-absorbent. For example, the sheet 4 may absorb less than 5 grams, or less than 3 gram or less than 1 gram or less than 0.5 gram of liquid, as measured by the test method WSP 10.1 (Section 7.2) "Liquid Absorptive Capacity".

Where the inner part is intended for use with a predetermined outer part 30 (see below), the total absorbent capacity of the sheet may be less than 1%, less than 0.2%, or less than 0.1% of the total absorbent capacity of the outer part 30 (see below).

In the embodiment shown, the fastening means are a pair of tape fasteners attached to the rear waist region, one on either side of the rear waist region. A variety of different types of fasteners may be used. The fasteners may include adhesive, for example adhesive tape, hook and loop type fasteners in two pieces, or fasteners including hook type fasteners that fasten directly to material such as the material of sheet 4. Any other fastener may also be used.

An opening 12 passes through the material 4 at a location that, in use, is adjacent to the wearer's anus. In the embodiment the opening is a slit 12 that extends longitudinally along the longitudinal centre line 14 of the embodiment. The opening, which may be in the form of the slit 12, may be positioned in the crotch region. In some embodiments, 10% or more, or 20% to 40%, or 30% or more of the length of the slit extends longitudinally from the midpoint towards the front waist region 6 and the remainder of the length of the slit extends rearwardly from the midpoint towards the rear waist region.

The dimensions and exact shape of the opening(s) may vary, depending on the size of the sheet 4 and/or the absorbent article. For example, in some embodiments, the opening is in the form of a slit opening with substantially parallel longitudinal side edges, which are connected in the front and back by V-shaped or rounded V-shaped (as shown herein) front and back edges, wherein both the front and back V-shaped edges comprise two angled edges. The maximum length of the slit opening may be for example 40% to 90%, or 50% to 80%, or about 60% to 70%, of the total length L of the absorbent article. The average width of the opening herein, in the stretched state, may be from 5% to 30%, or 10% to 25%, of the average width of the sheet 4 (including opening width), or for example for a size 4 diaper, 15 mm to 60 mm, or from 20 mm to 40 mm.

Elastic pieces 18, 20 extend longitudinally along either side of the slit 12 elasticating the sheet 4 in the region on either side of the slit. These may be formed as described in European Patent Publication EP1201212A2.

Although FIG. 1 shows such elastic regions 18, 20 as being relatively narrow they may, alternatively, extend over a greater width, and may in particular be up to the full width of the inner part.

Figure 2:
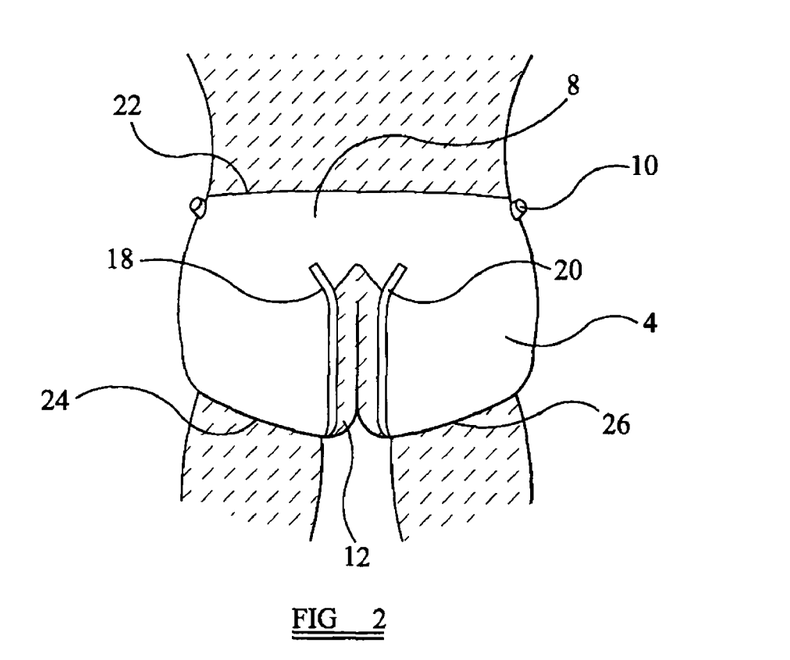
FIG. 2 shows a back view of a first embodiment of a diaper-type elasticated inner part as worn by a baby.

In use, the inner part 2 is placed around a wearer, here a baby, as illustrated in FIG. 2, the baby being shown shaded. The rear waist region 8 overlaps the front waist region 6. The fastening means 10 is used to join the front and rear waist portions 6, 8 on either side to fix the inner around the wearer. This forms a waist opening 22 and a pair of leg openings 24, 26. The slit 12 and elastic pieces 18, 20 pass between the leg openings.

As illustrated in FIG. 2, the elastic pieces 18, 20 act as cuffs holding the inner in place with the slit 12 being adjacent to the wearer's anus. The inner part 2 is held close and in place on the wearer's skin. The use of elastic minimises leaks. The elastic pieces 18, 20 thus constitute alignment means.

Figure 3:
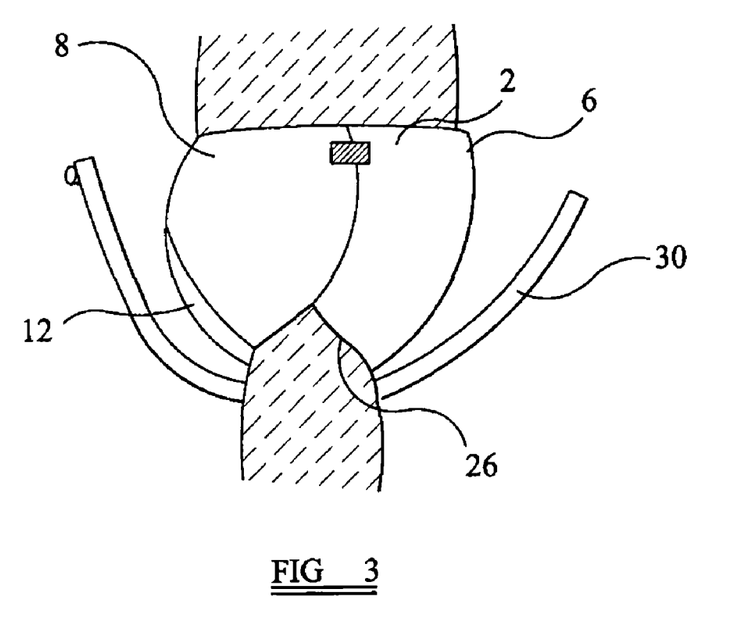
FIG. 3 illustrates a combination of elasticated inner and outer parts in side view.

Having fixed the inner part 2, an outer part 30 is then placed around the wearer and the inner part 2 (FIG. 3). The outer part 30 is, in this embodiment, a conventional diaper with a topsheet, absorbent core and backsheet. Such diapers are well known in the art and so will not be described further.

In use, BM passed by the wearer passes through the slit 12 and is captured by the outer part 30 and held between inner part 2 and outer part 30. Since the inner part 2 does not support the BM, it does not sag and remains held in place against the wearer's skin where it protects the wearer's skin from the BM held between inner part 2 and outer part 30.

A particular benefit of the inner part 2 in the form described is that it is relatively simple and hence cheap to manufacture.

In some embodiments, the sheet 4 has barrier properties. The barrier properties may be reflected in a hydrostatic head value, being the hydrostatic pressure supported by the non-woven sheet with a particular surface tension liquid. In the method set out below, that surface tension is 49 mN/m. The hydrostatic head (as measured by the method set out below) may be at least 18 mbar, at least 20 mbar, at least 25 mbar, or at least 30 mbar.

Alternatively or additionally, the sheet 4 may have a low surface tension strike through value of at least 30 seconds or at least 55 seconds. However, it is not required that the material of the sheet 4 be wholly impermeable. Instead of the use of a barrier non-woven, alternative materials may be used for sheet 4. For example, a fully elasticated material could be used, for example Lycra™, or elasticated non-wovens. In some cases, it may be possible to dispense with the need for elastics 18, 20 making the inner part 2 still cheaper and easier to manufacture. In that case, the elasticity of the elasticated material itself may ensure that the longitudinal regions of the sheet 4 adjacent to the slit 12 are elastic regions to hold the sheet 4 in place with the slit 12 correctly aligned.

In some embodiments, the sheet 4 of the inner part may be air-permeable. This can assist the comfort of the user and to reduce the risk of skin problems. The sheet 4 may have an air permeability of at least 3 Darcy/mm, at least 5 Darcy/mm, at least 10 Darcy/mm, at least 20 Darcy/mm, or even at least 30 Darcy/mm. This can be determined by the method set out below.

Alternatively, the material of sheet 4 may be an impermeable plastic sheet. This approach may be relatively low cost. The sheet may be apertured, with many small perforations to be breathable for increased comfort.

In some embodiments, the sheet is made of a hydrophobic material to increase wearer comfort. In some instances, BM mixed with urine can have very low surface tension, e.g. of about 25 to 30 mN/m. The surface energy of the sheet or part thereof, e.g. the inner surface of the sheet 4, may be less than 28 mN/m, less than 24 mN/m, and less than 20 mN/m. The low surface energy of the sheet may in particular be reflected by a very high alcohol repellency value, measured by the test as set out below. The mean alcohol repellency of the sheet 4 may be at least 7.0, at least 8.0, at least 9.0, or at least 10.0.

The sheet 4 may be coated with an agent to make it more hydrophobic, kind to the skin, or may be coated with a lotion. Suitable agents include fluorocarbons as described in U.S. Pat. No. 5,876,753, issued to Timmons et al. on Mar. 2, 1999; U.S. Pat. No. 5,888,591 issued to Gleason et al. on Mar. 30, 1999; and U.S. Pat. No. 6,045,877 issued to Gleason et al. on Apr. 4, 2000. Other agents include silicone. Useful methods for applying the agent to the topsheet, without reducing the air permeability, can be found in U.S. Pat. No. 5,322,729 and PCT Publication No. WO 96/03501. The agent is most effectively applied to fibrous non-woven web, which comprising thermoplastic polymer fibers, which may be selected from the group comprising: polyolefins, polyesters, polyurethanes, and polyamides, wherein the thermoplastic polymer may be a polyolefin, a polypropylene, or a polyethylene.

The sheet 4 may be at least partially treated with a chemical, which lowers the surface energy of the topsheet, which chemical may be referred to as masking facilitating agent. To obtain sheets 4 with low surface energy and high alcohol repellency, one can use any method of applying masking facilitating agents. The method of applying the masking facilitating agent may be such that a very thin coating of agent is deposited on the sheet 4 or part thereof, and may be such that the air permeability and porosity is substantially unchanged.

The masking facilitating agent may be topically applied to a fibrous web or the masking facilitating agent may be added in molten state to the compound(s) used to make the topsheet, e.g. to the fibers, prior to formation of the topsheet web. Thus for example, if the topsheet is a non-woven material made of a fiber blend, this fiber blend can comprise a masking facilitating agent in molten state, that will provide the resulting non-woven with a high alcohol repellency and a low surface energy. The use of one or more melt-in masking facilitating agents may be combined with topical treatment with one or more masking facilitating agent, as mentioned above. Agents may be selected from the group comprising fluorocarbons, siloxanes, polysiloxanes, preferably including fluorinated monomers and fluorinated polymers, including hexafluoroethylene, hexafluoropropylene and vinyl fluoride and vinylidene fluoride, fluoroacrylate and fluoromethacrylate. The topsheet may be provided with poly (tetra) fluoroethylene, fluorinated ethylene-propylene copolymers and/or fluorinated ethylene-tetrafluoroethylene copolymers masking facilitating agent.

The sheet 4 may be made of a multilayer laminate. For example, the laminate may include an inner layer of soft material and an outer impermeable layer. The inner layer may be a non-woven chosen for its comfort.

Modifications to the inner part 2 are possible. For comfort, the waist bands 6, 8 may be elasticated. Further, the fastening means 10 need not be attached directly to sheet 4, but tabs may be provided depending laterally from sheet 4; if desired, these tabs may be elasticated. Alternatively, a drawstring may be provided along one or both of the front and rear waist regions 6, 8 or around the opening 12.

Figure 4:
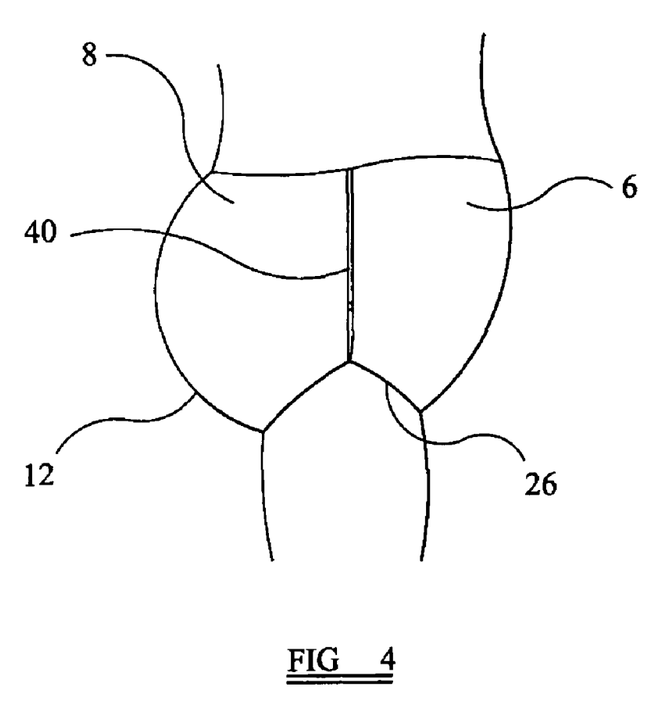
FIG. 4 shows a second embodiment of a pants-like elasticated inner part.

FIG. 4 shows an alternative configuration in which the inner part 2 is "pants-like". In this case, side seams 40 join front and rear waist regions 6, 8 together. In the embodiment shown, the side seam extends from the waist to the leg opening 26. Such a "pants-like" inner is particularly convenient in combination with "training pants" as the outer diaper. Such an article may be manufactured using a blank similar in form similar to that shown in FIG. 1 without the fastening means 10 and forming the pants-like inner using similar folding apparatus to that used to manufacture pants-type diapers known in the art.

By putting on the inner part 2 first and then the outer part 30, the inner part 2 can be placed accurately in position to provide the maximum protection ensuring that the slit 12 is correctly located.

Figure 5:
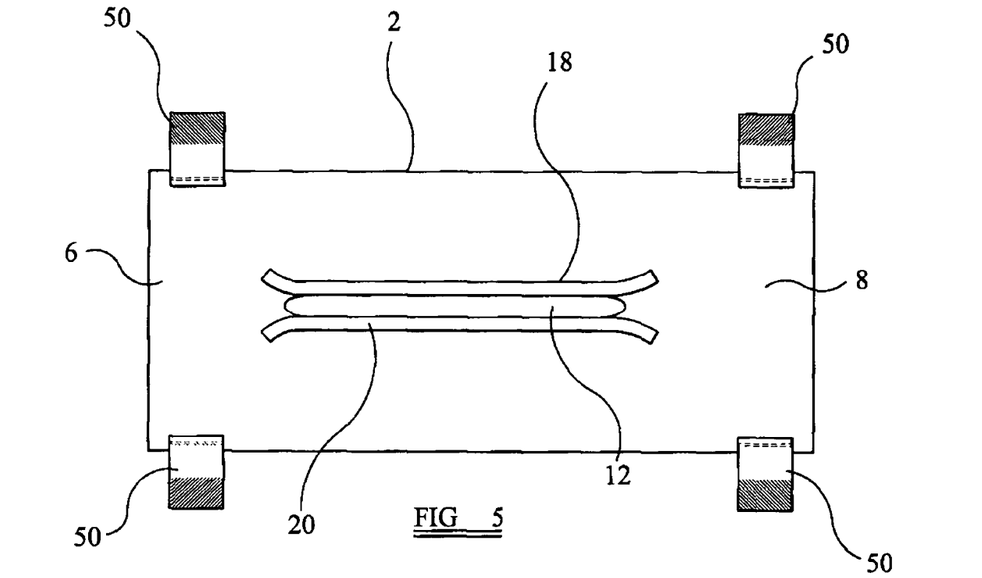
FIG. 5 shows a view of a third embodiment an alternative inner part.

Instead of simply wearing the inner part 2 and then putting on the outer part 30, an alternative approach is to fix the inner part 2 to the outer part 30 and then put the combination of inner and outer on the wearer. FIG. 5 illustrates an inner in this form which has fastening tabs 50 provided on both the front and rear waist bands 6, 8 and on both sides of the inner. In use, as illustrated schematically in FIG. 6, these fastening tabs 50 are used to fix the inner part 2 to outer part 30. The front waist region 6 of the inner is attached to the front waist region 52 of the outer, and the rear waist region 8 of the inner is attached to the rear waist region 54 of the outer. For example, hook-type fasteners may be used as fastening tabs 50 and these may engage with non-wovens used as the topsheet on the outer part 30. Adhesive tabs, hook and loop type fasteners, and indeed any other fastener may be used as required.

Figure 6:
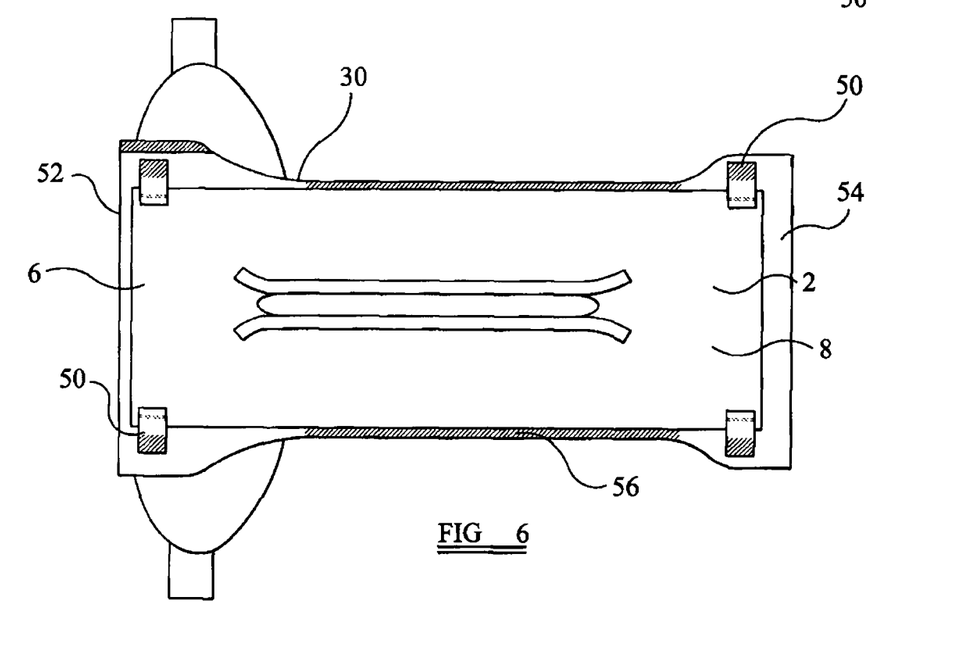
FIG. 6 illustrates the inner part of the third embodiment fixed to an outer.

The diaper illustrated in FIG. 6 has elasticated leg cuffs 56. In the embodiment the inner extends laterally as far as the cuffs so the cuffs 56 seal the outer to the inner at the leg openings 24, 26. The inner can be wider than the outer to enhance this sealing.

The outer part 30 may have leg cuffs. In some embodiments, the inner part 2 and outer part 30 may be sized so that the leg cuffs of outer part 30 seal against the inner part 2 and not the wearer's skin. This may be achieved, for example, by making the width of the inner greater than the width of the outer measured at the mid point 16 of each of the inner and outer.

In some embodiments, when the inner and outer are aligned with the mid point of the inner on the mid point of the outer and with the longitudinal directions of inner and outer parallel, the width of the inner may be greater than the width of the outer over the full length of the slits 12. Note that this relationship between the width of inner part 2 and outer part 30 is applicable not just for an inner part of the type shown in the third embodiment that is intended to be fixed to the outer part before putting the two together on a wearer but to other types such as pants-type or diaper like inner parts as well.

Although separate fasteners 50 are shown on either side of the inner waist regions 6, 8, the fasteners 50 may in alternative embodiments extend laterally along the front and rear waist regions on the outside of the inner to attach the inners 6, 52 and outers 8, 54 together along a significant fraction of the length.

Figure 7:
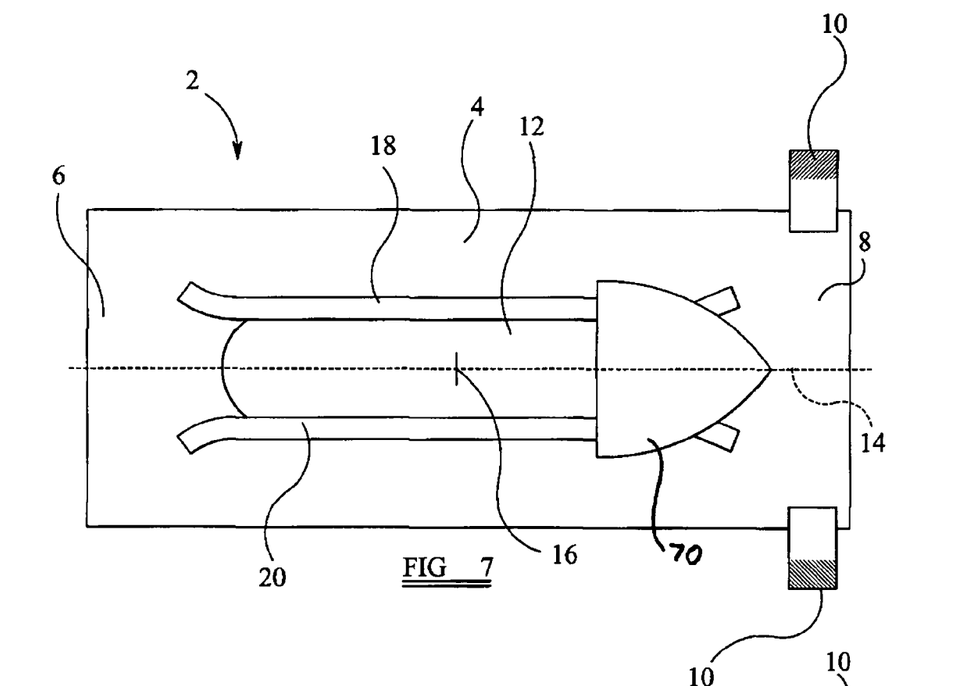
FIG. 7 illustrates an inner part of a fourth embodiment.

As illustrated in FIG. 7, a further embodiment includes genital protection. Genital coversheet 70 is mounted over the slit 12 at the front end of the slit on the outer surface of the sheet 4 of inner part 2. In use, the genital coversheet 70 covers the wearer's genitals. The genital coversheet 70 is intended to impede BM contained between the inner part 2 and outer part 30 parts from coming into contact with the wearer's genitalia and hence the genital coversheet 70 reduces soiling of the genital region. One or more longitudinal folds may be provided in genital coversheet 70 to form a pocket. The genital coversheet 70 may be urine permeable. It may be hydrophilic, and has a low rewet. The caliper of the coversheet 70 may be 0.5 mm to 1.5 mm measured under a compression of 0.3 psi. Materials may include spunbond nonwovens, laminates of spunbond nonwovens and meltblown nonwovens, as well as carded nonwoven materials. Alternative embodiments use an apertured formed film for the genital coversheet 70. Suitable examples are described in PCT Publication No. WO96/00549.

Figure 8:
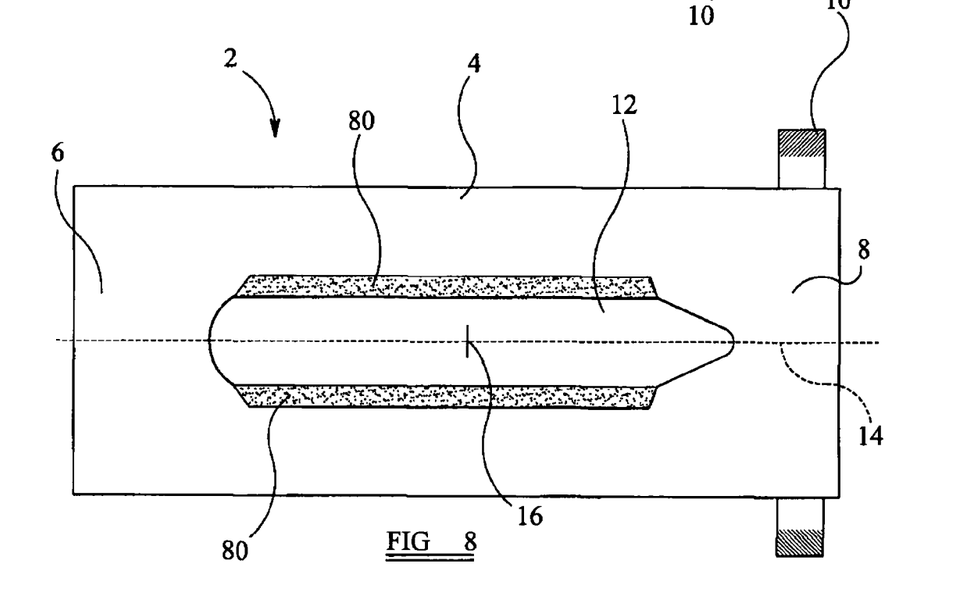
FIG. 8 illustrates an inner part of a fifth embodiment.

A fifth embodiment is illustrated in FIG. 8, which shows the inner surface of the inner part 2. In this embodiment, temporary fixing adhesive 80 is formed in strips along the edges of the opening 12. In use, the adhesive fixes the inner part to the wearer ensuring an excellent seal between inner part 2 and wearer. The adhesive 80 also constitutes alignment means. The adhesive may be used in addition to elastics 18, 20 or instead of the elastics. The outer part may be a conventional diaper or a modified conventional diaper, for example having landing regions defined to which the inner part can be attached.

Figure 9:
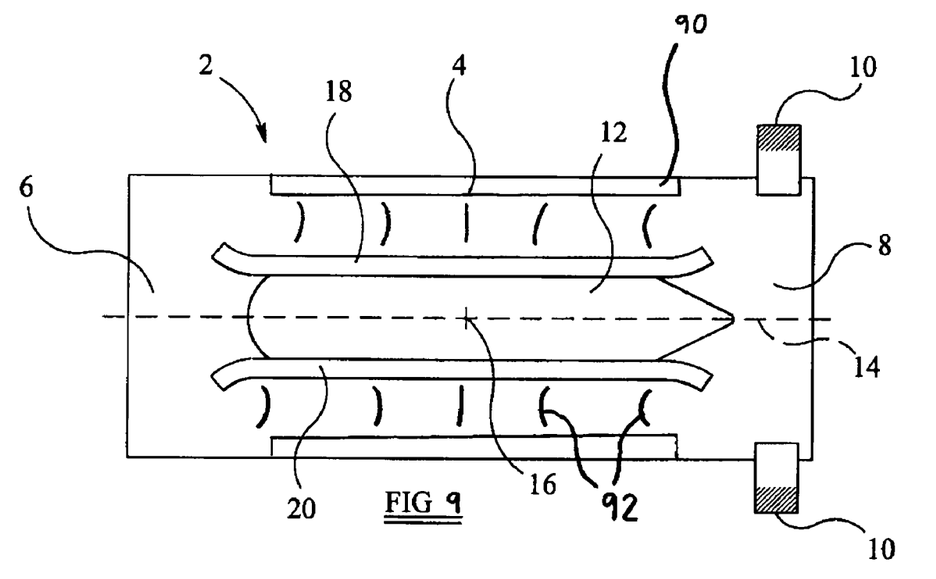
FIG. 9 illustrates an inner part of a sixth embodiment.

FIG. 9 illustrates a further modification. In this case the inner part 4 includes inner leg elastics 90 on the outer longitudinal edges of the inner part. These leg elastics improve the fit and sealing in the leg region. Further, additional elastics 92 are provided between the outer longitudinal edges and the opening 12, these additional elastics being provided for shaping the inner part 4. In other respects, the inner part of this arrangement is the same as the embodiment of FIG. 1.

Although the leg elastics 90 and additional elastics are here shown in combination with the embodiment of FIG. 1, those skilled in the art will appreciate that such leg elastics and additional elastics can also be used separately or in combination, as well as being incorporated in other embodiments.

Since the inner part 2 carries out many of the functions of the topsheet on a conventional diaper, the inner part 2 may be used with a modified conventional diaper with the topsheet omitted.

Although particular embodiments of the present invention have been described and illustrated, those skilled in the art will appreciate that various changes and modifications may be made within the scope of this invention. Further, features of the various embodiments may be combined. For example, instead of a single opening there may be a number of openings in the inner part, for example one opening next to the anus in use and another in the genital region. Further, various features described with reference to one embodiment may also be applied in other embodiments, as will be appreciated by those skilled in the art.

The various measurement methods used will now be described.

Air Permeability

The air permeability is determined by measuring the time in which a standard volume of air is drawn through the test specimen at a constant pressure and temperature. This test is particularly suited to materials having relatively high permeability to gases, such as preferred herein, in particular nonwoven materials.

A Tex Test FX3300 instrument is used. The Test Method conforms to ASTM D737. The test is operated in a laboratory environment typically about 22±2° C. and about 35%±15% relative humidity. The test specimen has to be conditioned for at least 2 hrs. The test pressure is 125 Pascals and the test area is 38 $c^2$. In this test, the instrument creates a constant differential pressure across the sample, which draws air through the sample. The rate of air flow through the sample is measured in $ft^3/min/ft^2$ and converted to permeance (in Darcy/mm) according to the Darcy's Law:

$$K/d(\text{Darcy/mm}) = (V \cdot \mu)/(t^* A^* \Delta p)$$

wherein k is the permeability per unit area of the specimen; V/t is the volumetric flow rate in $cm^3/sec$; μ is the viscosity of air ($1.86*10^{-5}$ Pa sec); d is the test material thickness in mm; A is the cross sectional area of the specimen in $cm^2$; Δp is the pressure differential in Pascal or Pa; and 1 Darcy=$9.869*10^{-9}$ $cm^2$.

For each sample, three replicates are run, and the mean result of the three samples is reported as air permeability herein.

Hydrostatic Head (Hydrohead)

The hydrostatic head (also referred to as hydrohead) as used herein is measured with a relatively low surface tension liquid, for this test. a 49 mN/m liquid (solution).

This liquid is prepared as set out below.

This test is performed as set out in co-pending PCT Publication No. WO2005/112854A, conforming to the Inda/Edana test WSP 80.6 (05). However, the water pressure (from below) is increased with a rate is 60 mbar/min.

A sample of 5 $cm^2$ is taken from the sheet. The sample should be free from elastic material or edges that are connected to other materials.

The test head used has a 2.5 cm diameter; the protective sleeve used has a 2.2 cm diameter.

The test is performed on this sample and the Hydrostatic head value is obtained, and referred to herein.

49 mN/m (dynes/cm) Liquid Preparation:

A 10 liter canister with tap is cleaned thoroughly 3 times with 2 liters polyethylene and then 3 times with 2 liters distilled/deionized water. Then, it is filled with 10 liters distilled/deionized water and stirred with a clean stirring bar for 2 h, after which the water is released via the tap. A 5 liter glass is cleaned 6 times with water and then 6 times with distilled/deionized water. Then, 30.00 g of Na Cholate and 5 liters of distilled/deionized water are placed in the cleaned 5 liters glass. (NaCholate should have a TLC purity of >99%, e.g. supplied by Calbiochem, catalog #229101). This is stirred with a clean stirring bar for about 5 min, until the Na Cholate is visibly dissolved. The stirring bar is removed from the glass with a magnetic stick (without touching the solution) and then the Na cholate solution is poured into the 10 liters canister and more distilled/deionized water is added such that the concentration of the final solution is 3 g/l. This is further stirred with a stirring bar for 2 hours and then used.

This preparation of the solution and use thereof is at the temperature stated for the test for which it is used, or if no temperature is stated, it is kept at 20° C.

The surface tension of the solution is measured and this should be 49 mN/m (±2). (The surface tension may be determined by method: ASTM D1331-56 ("Standard test method for surface and interfacial tension of solution of surface active agents") using a Kruss K12 tensiometer.)

Low Surface Tension Strike Through Value Method

The low surface tension strike through value referred to herein may be obtained by the Edana method WSP70.3 (05), except that a low surface tension liquid (see below) is used and a sample of 1 inch×1 inch (25 mm×25 mm) may be used. The sample should be free of elastic material or of edges that are connected to other materials.

The value obtained from this sample measurement is reported herein.

For this test, the low surface tension liquid is a liquid with a surface tension of 32 mN/m prepared as follows:

In a clean flask, 2.100 grams of Triton-X-100 is added to 500 ml distilled water (already in flask) and then 5000 ml distilled water is added. The solution is mixed for 30 minutes and then the surface tension is measured, which should be 32 mN/m.

The surface tension may be determined by method: ASTM D1331-56 ("Standard test method for surface and interfacial tension of solution of surface active agents") using a Kruss K12 tensiometer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
    an inner part including a sheet of material having an inner side, an outer side opposite the inner side, a front waist region, and a rear waist region, wherein the front waist region is connected with the rear waist region to form a waist opening and two leg openings;
    an outer part including an absorbent material and adapted for wearing in the region of a wearer's anus, the outer part being separate from the inner part and adapted to be worn over the outer side of the inner part such that the inner part can be worn independently of the outer part;
    fastening tabs connected with the front and rear waist regions of the inner part, the fastening tabs adapted to releasably connect directly with the outer part; and
    an opening in the sheet of material of the inner part for allowing bowel movement waste to pass through the opening so that the inner part cooperates with the outer part in use to collect and retain bowel movement waste between the inner and outer parts.

2. The disposable absorbent article of claim 1, further comprising adhesive disposed along an edge of the opening adapted to adhesively fix the inner part to a wearer for maintaining the opening in alignment with the wearer's anus in use.

3. The disposable absorbent article of claim 2, further comprising a genital coversheet attached to the inner part over a portion of the opening for covering a wearer's genitals in use.

4. The disposable absorbent article of claim 1, further comprising elastic regions disposed along an edge of the opening for maintaining the opening in alignment with the wearer's anus in use.

5. The disposable absorbent article of claim 4, further comprising a genital coversheet attached to the inner part over a portion of the opening for covering a wearer's genitals in use.

6. The disposable absorbent article of claim 1, wherein the outer part is releasably fastenable to the outer side of the inner part.

7. The disposable absorbent article of claim 1, wherein the outer part has leg openings and elastic cuffs around the leg openings, wherein the inner and outer parts are sized so that, in use, the elastic cuffs of the outer part engage the leg openings of the inner part.

8. The disposable absorbent article of claim 1, wherein the inner part includes a pair of permanent seams attaching the front waist region to the rear waist region to form a pants-like inner part, in which the opening is a slit located between the leg openings.

9. The disposable absorbent article of claim 1, wherein the inner part includes fasteners attached to one of the front waist region and the rear waist region, the fasteners being adapted to connect with the other of the front waist region and rear waist region.

10. The disposable absorbent article of claim 1, wherein the sheet of material of the inner part has a hydrostatic head value of 18 mbar or greater, measured using a liquid with a surface tension of 49 mN/m.

* * * * *